(12) United States Patent
Podlesak et al.

(10) Patent No.: US 8,725,428 B2
(45) Date of Patent: May 13, 2014

(54) DEVICE AND SYSTEM TO RECONSTRUCT TRAVEL HISTORY OF AN INDIVIDUAL

(75) Inventors: David W. Podlesak, White Rock, NM (US); James R. Ehleringer, Salt Lake City, UT (US); Thure E. Cerling, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 728 days.

(21) Appl. No.: 12/919,446

(22) PCT Filed: Feb. 25, 2009

(86) PCT No.: PCT/US2009/035118
§ 371 (c)(1),
(2), (4) Date: Feb. 7, 2011

(87) PCT Pub. No.: WO2009/108687
PCT Pub. Date: Sep. 3, 2009

(65) Prior Publication Data
US 2011/0125413 A1  May 26, 2011

Related U.S. Application Data

(60) Provisional application No. 61/031,189, filed on Feb. 25, 2008, provisional application No. 61/036,847, filed on Mar. 14, 2008.

(51) Int. Cl.
*G01N 33/497* (2006.01)
*G06F 17/40* (2006.01)
*G06F 19/00* (2011.01)

(52) U.S. Cl.
CPC .............. *G01N 33/497* (2013.01); *G06F 17/40* (2013.01); *G06F 19/00* (2013.01)
USPC .................. 702/24; 73/23.2; 702/1; 702/127; 702/187; 702/189

(58) Field of Classification Search
CPC .......... A61B 5/00; A61B 5/08; A61B 5/5082; A61B 2010/00; A61B 2010/0083; A61B 2010/0087; G01D 7/00; G01D 21/00; G01N 33/00; G01N 33/004; G01N 33/48; G01N 33/483; G01N 33/497; G01N 2033/00; G01N 2033/0004; G01N 2033/48; G01N 2033/483; G06F 11/00; G06F 11/30; G06F 11/32; G06F 17/00; G06F 17/40; G06F 19/00
USPC ........... 73/23.2, 23.3, 432.1, 865.8; 600/300, 600/529, 543; 702/1, 22, 23, 24, 127, 187, 702/189; 708/100, 105, 200
IPC ... A61B 5/00,5/08, 5/082, 2010/00, 2010/0083, A61B 2010/0087; G01D 7/00, 21/00; G01N 33/00, 33/004, 33/48, 33/483, 33/497, 2033/00, G01N 2033/0004, 2033/48, 2033/483, 2033/497; G06F 11/00, 11/30, 11/32, 17/00, 17/40, G06F 19/00
See application file for complete search history.

(56) References Cited

U.S. PATENT DOCUMENTS 6,656,127 B1  12/2003  Ben-Oren et al.
6,778,269 B2 *  8/2004  Fink et al. ..................... 356/301

(Continued)

FOREIGN PATENT DOCUMENTS

EP        0556614        8/1993
KR    10/2002/0085379    11/2002

OTHER PUBLICATIONS

Alstad et al.; Environmental Controls on the Carbon Isotope Composition of Ecosystem-Respired CO2 in Contrasting Forest Ecosystems in Canada and the USA; Tree Physiology; 2007; vol. 27; pp. 1361-1374.

(Continued)

*Primary Examiner* — Edward Cosimano
(74) *Attorney, Agent, or Firm* — Thorpe North & Western LLP (57) ABSTRACT

Methods and systems for determining travel history can be based on noninvasive analysis of stable isotope ratios in the body of an individual. A method for reconstructing a travel history for an individual can include collecting a sample of exhaled breath from the individual and analyzing the sample to obtain a breath isotope ratio. The breath isotope ratio can be transformed to a body water isotope ratio and compared to a map model correlating input isotope ratios to geographic locations so as to determine a travel origin for the individual.

22 Claims, 7 Drawing Sheets

(56) References Cited

U.S. PATENT DOCUMENTS

| | | |
|---|---|---|
| 7,488,229 B2* | 2/2009 | Ben-Oren et al. ............... 445/23 |
| 2003/0053049 A1 | 3/2003 | Fink et al. |
| 2003/0216660 A1* | 11/2003 | Ben-Oren et al. ............ 600/532 |

OTHER PUBLICATIONS

Appenzeller et al.; Stable Isotope Ratios in Hair and Teeth Reflect Biologic Rhythms; PLOS One; Jul. 2007; Issue 7; pp. 1-6.

Bowen et al.; Stable Isotope Ratios of Tap Water in the Contiguous United States; Water Resources Research; Mar. 15, 2007; vol. 43; pp. 1-12.

Cerling et al.; Determining Biological Tissue Turnover Using Stable Isotopes: The Reaction Progress Variable; Oecologia; Dec. 21, 2006; vol. 151; pp. 175-189.

Cryan et al.; Stable Hydrogen Isotope Analysis of Bat Hair as Evidence for Seasonal Molt and Long-Distance Migration; Journal of Mammalogy; 2004; vol. 85 No. 5; pp. 995-1001.

Human; CU Laser Device Analyzes Breath to Detect Disease; denverpost.com, The Denver Post; Feb. 19, 2008; 2 pages; denverpost.com/news/ci_8298919.

Lai et al.; Seasonal and Interannual Variations of Carbon and Oxygen Isotopes of Respired $CO_2$ in a Tallgrass Prairie: Measurements and Modeling Results from 3 Years with Contrasting Water Availability; Journal of Geophysical Research; 2006; vol. 111; pp. 1-14.

Macko et al.; Documenting the Diet in Ancient Human Populations Through Stable Isotope Analysis of Hair; Phil. Trans. R. Soc. Lond.; 1999; vol. 354; pp. 65-76.

Podlesak et al.; Turnover of Oxygen and Hydrogen Isotopes in the Body Water, $CO_2$, Hair, and Enamel of small Mammal; Geochimica et Cosmochimica Acta; 2008; vol. 72; pp. 19-35.

Water-Vapor Isotope Analyzer; lgrinc.com/Index.asp?subid=pc &ProductLineID=1&Produ . . . ; as accessed on Feb. 20, 2009.

Water-Vapor Isotope Analyzer; ://lgrinc.com/Index.asp?subid=ps &Product CategoryID=15; as accessed on Feb. 20, 2009.

Ehleringer et al.; Hydrogen and Oxygen Isotope Ratios in Human Hair are Related to Geography; PNAS; Feb. 26, 2008; vol. 150, No. 8; pp. 2788-2793.

* cited by examiner

DEVICE AND SYSTEM TO RECONSTRUCT TRAVEL HISTORY OF AN INDIVIDUAL

RELATED APPLICATIONS

This application claims the benefit of U.S. Provisional Application No. 61/031,189, filed Feb. 25, 2008, entitled "Device and System to Reconstruct Travel History of an Individual using the Stable Isotope Analysis of Breath," and U.S. Provisional Application No. 61/036,847, filed Mar. 14, 2008, entitled "Device and System to Reconstruct Travel History of an Individual," each of which is incorporated herein by reference.

BACKGROUND

The stable isotope composition of many materials are known to be useful in determining the history or geographic origins of those materials. Similarly, the stable isotope composition of body water and body tissues are commonly used to investigate movement patterns of humans and animals. For example, isotope ratios in hair, bone and teeth have been used to identify the location of origin for unknown samples and to track migration and resource use in modern and ancient human populations. As a result, samples of tissues such as hair have been used to predict regions of origin for these samples. There remains, however, a need for more conveniently and efficiently ascertaining recent travel history of individuals. In particular, ways of quickly obtaining travel origin information from samples that may be gleaned noninvasively would greatly forward this art. Such approaches can provide a great benefit to efforts such as forensics and security.

SUMMARY

Methods and systems for determining travel history can be based on noninvasive analysis of stable isotope ratios in the body of an individual. A method of reconstructing a travel history for an individual can comprise collecting a sample of exhaled breath from the individual; analyzing the sample to obtain a breath isotope ratio for at least one isotope; transforming the breath isotope ratio to a body water isotope ratio; and determining a travel origin for the individual by comparing the body water isotope ratio to a map model correlating input isotope ratios to geographic locations.

Another general embodiment sets forth a system for reconstructing a travel history for an individual, comprising a collection device configured to collect a sample of breath from the individual; an analysis device configured to accept the sample of breath and provide a measurement of a breath isotope ratio for at least one isotope; and a data processor configured to accept the measurement from the analysis device. The data processor is capable of transforming each breath isotope ratio to a body water isotope ratio and comparing the body water isotope ratio to a map model correlating isotope ratios to geographic locations so as to determine a travel origin for the individual. An output device is also associated with the data processor to communicate the calculated travel origin.

Another general aspect provides a computer readable data storage medium having computer readable code embodied thereon for determining a travel origin for an individual based on an isotope ratio for an isotope measured in the breath of the individual. The code comprises an input routine for receiving isotope ratio data in the form of breath isotope ratio measurements and a time interval; a transformation routine for transforming the isotope ratio data into body water isotope ratios, wherein the transformation routine includes a body water model correlating breath isotope ratio measurements to body water isotope ratios; and an output routine for comparing the body water isotope ratio to a map model correlating isotope ratios to geographical locations, and configured to output the travel origin.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

DETAILED DESCRIPTION OF EXAMPLE EMBODIMENTS

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

It must be noted that, as used in this specification and the appended claims, the singular forms "a," "an," and "the" include plural referents unless the context clearly dictates otherwise. Thus, for example, reference to "a sample" includes one or more of such materials, and reference to a "correlating" step includes reference to one or more of such steps.

DEFINITIONS

In describing and claiming the present invention, the following terminology will be used in accordance with the definitions set forth below.

As used herein, "substantially" or "substantial" refers to the complete or nearly complete extent or degree of an action, characteristic, property, state, structure, item, or result. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result.

As used herein, "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited.

As an illustration, a numerical range of "about 10 to about 50" should be interpreted to include not only the explicitly recited values of about 10 to about 50, but also include individual values and sub-ranges within the indicated range. Thus, included in this numerical range are individual values such as 20, 30, and 40 and sub-ranges such as from 10-30, from 20-40, and from 30-50, etc. This same principle applies to ranges reciting only one numerical value. Furthermore, such an interpretation should apply regardless of the breadth of the range or the characteristics being described.

As used herein, stable isotope ratios are reported in δ-notation as parts per thousand (‰) deviations from an international standard according to the equation:

$$\delta = (R_{sample}/R_{standard} - 1) \times 1000 \quad [1]$$

where $R_{sample}$ is the corresponding ratio ($^2H/^1H$, $^{13}C/^{12}C$, $^{18}O/^{16}O$) of the sample and $R_{standard}$ is the isotope ratio of the standard. Isotope fractionation is the difference between two phases in equilibrium:

$$\alpha_{BC} = R_B/R_C = (1000 + \delta_B)/(1000 + \delta_C) \quad [2]$$

and isotope enrichment is:

$$\epsilon_{BC} = (\alpha_{BC} - 1) \times 1000 \quad [3]$$

Isotope fractionation at equilibrium are expressed as $\alpha_{BC}$ and $\epsilon_{BC}$ and $\alpha_{BC}^*$ and $\epsilon_{BC}^*$ as isotope difference (non-equilibrium).

Methods and systems for determining travel history can be based on a noninvasive analysis of stable isotope ratios in the body of an individual. Reconstructing a travel history for an individual can ascertain the isotope ratios present in the body of the individual non-invasively by obtaining from said individual a sample, the composition of which is indicative of the individual's internal isotopic composition. Another advantage of using breath samples is that multiple samples may be obtained from one individual without ill effect. Accordingly, this embodiment can comprise the steps of collecting a sample of exhaled breath from the individual and analyzing the sample to obtain a breath isotope ratio for at least one isotope.

The usefulness of sampling isotopes excreted by an individual in tracing travel histories can be realized in working models of the isotopic composition of water in the body. Such models allow one to express how isotope composition of excreta can relate to body water composition, as well as how either of those values can relate to various sources of isotope intake. The latter consideration in particular provides valuable information in that such isotope inputs tend to vary with geographic location.

Figure 1:
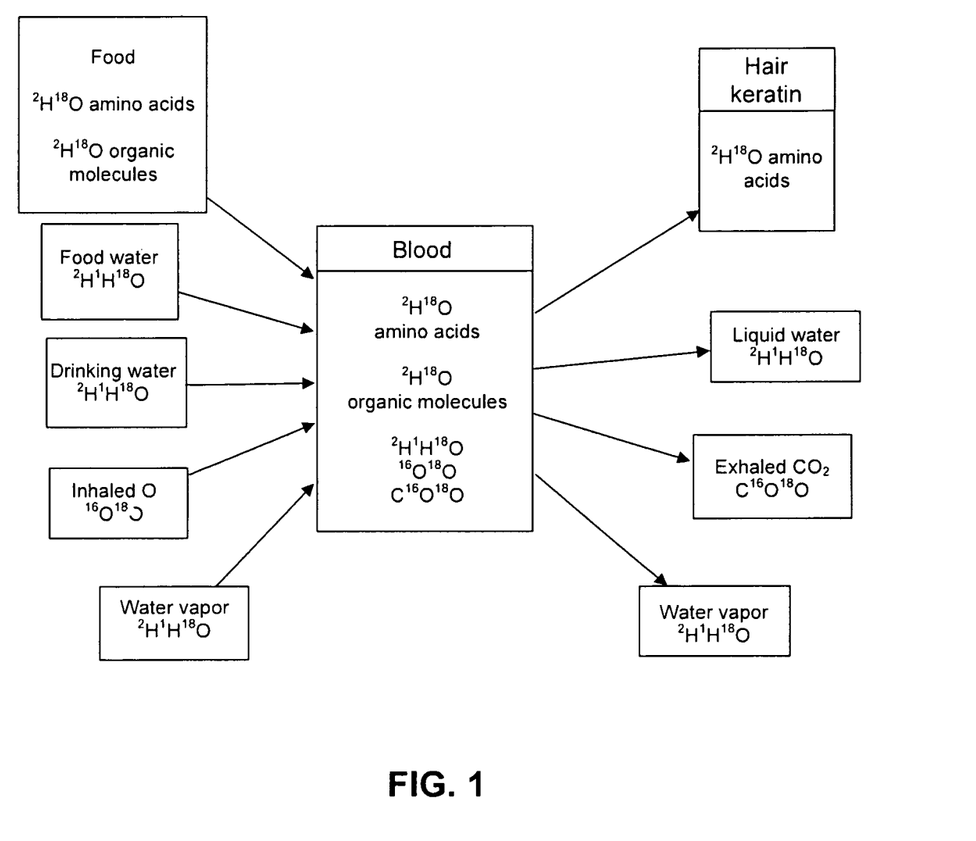
FIG. 1 shows a box-and-arrow diagram of a steady-state hair keratin model. Box-arrow model of the important physiological and biochemical factors that influence the hydrogen and oxygen stable isotope composition of keratin in human hair under steady-state conditions.

The breath isotope ratio can be transformed to a body water ratio. The correlation between isotope ratios measured in the breath or any other secretion or excretion to the isotope ratio of the body water as a whole can be reflected in models relating body water isotope ratios to various isotope inputs and outputs. An exemplary model for hydrogen and oxygen isotopes is represented by the box-and-arrow diagram shown in FIG. 1. This model can be a steady-state model, which assumes that the individual is in equilibrium with his/her diet and drinking water, and that changes in diet or drinking water sources have not occurred during the recent past. As shown in the diagram, there are multiple inputs and outputs of oxygen and hydrogen to body water that can be incorporated into the model. Suppliers of hydrogen and/or oxygen include food, free water in food, hydrogen and oxygen bound in organic food molecules, drinking water, atmospheric oxygen and atmospheric water vapor. Outputs of hydrogen and/or oxygen include liquid water in the form of urine and sweat, water vapor loss associated with breathing and carbon dioxide loss.

Figure 2:
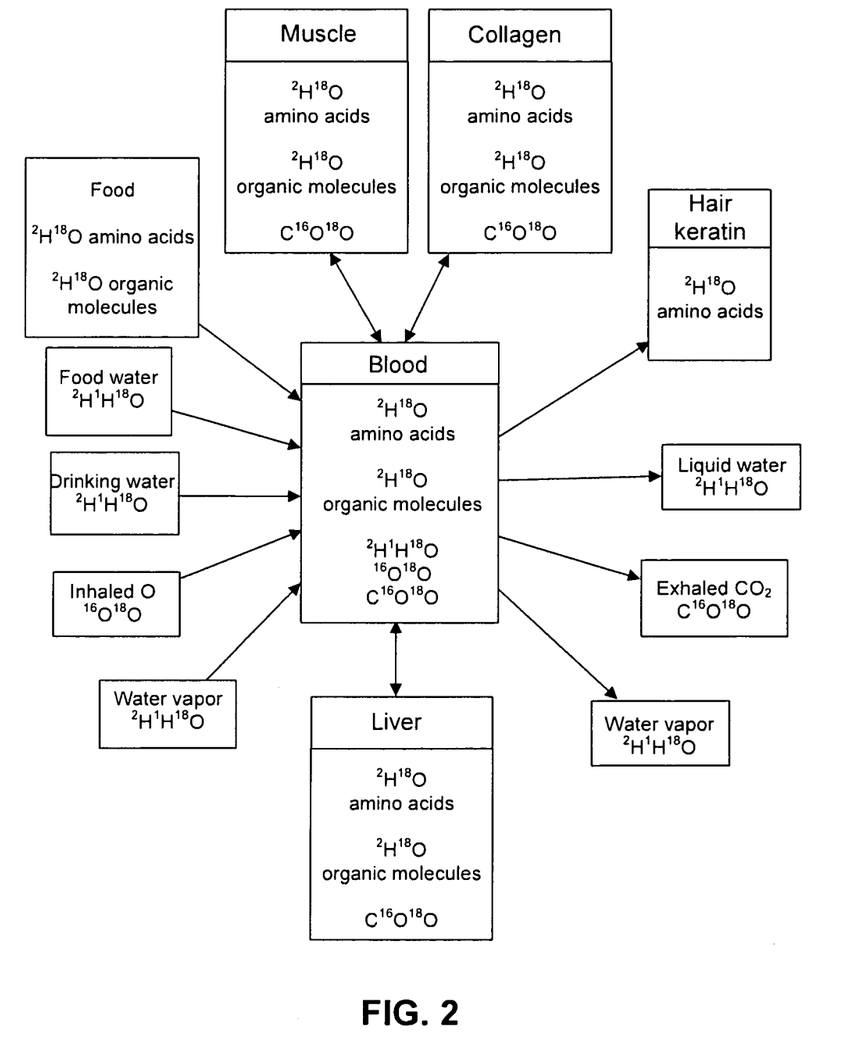
FIG. 2 shows a box-arrow diagram model of the physiological and biochemical factors that can influence the hydrogen and oxygen stable isotope composition of keratin in human hair for persons that may not be in isotopic equilibrium with their current diet and drinking water.

In addition to a steady state component, a process for determining travel history can also benefit from the inclusion of a transient component to deal with the influence of tissue turnover (primarily muscle and liver tissues) on the isotopic signature of samples. Tissues are continually degraded and rebuilt within humans. In addition, as a consequence of moving from one region to another, the hydrogen and oxygen in an individual's breath sample may not be in immediate isotopic equilibrium with the diet and drinking water in the new location. During that period of time, both dietary inputs and muscle and liver tissues may act as sources of oxygen and hydrogen contributing to body water composition. At the same time, the various tissues draw from the body water reservoir of isotopes in new growth. These relationships are reflected in the box-and-arrow diagram shown in FIG. 2. Thus, when individuals move between regions, the turnover of tissue (liver, muscle, collagen) will, in part, determine the pattern of isotopes recorded in breath. A non-steady-state model of stable isotope ratios in breath that incorporates both the influences of dietary input and tissue turnover can contribute to a more accurate reconstruction of the movements of individuals. A demonstration of the usefulness of such models has been shown in Podlesak et al., "Turnover of oxygen and hydrogen isotopes in the body water, $CO_2$, hair and enamel of a small mammal after a change in drinking water," *Geochimica et Cosmochimica Acta,* 72:19-35 (2007), which is incorporated herein by reference.

A model of isotope turnover can be used to account for the time elapsed since an individual left a particular location, over said time the individual's isotope composition has changed in the course of moving toward equilibrium with the present environment. As a result of turnover, a measurement of isotope ratios in a breath sample can reflect not only the individual's prior location but the changes in their isotope composition arising from any difference between their prior location and their present one and the time spent in the latter.

Therefore, the present embodiment can include adjusting a breath isotope ratio to account for turnover that has occurred since the individual left their last location. The adjustment value may be reached by employing an appropriate isotope turnover model in order to determine a rate of turnover. In combination with a known or suspected time since the individual changed locations, this rate can be used to generate an adjusted breath isotope ratio measurement that corresponds to the likely body isotope composition achieved by the individual at the previous location.

In one aspect, this may facilitate extrapolation of a present breath isotope ratio to that of some time in the recent history of the individual in order to arrive at likely geographic locations for the individual at that time. In an alternative embodiment, this approach may be used to corroborate or disprove a travel history attested to by an individual, in which the adjusted isotope ratio is compared to that which would be expected in an individual in equilibrium with the attested original location. In accordance with this embodiment, a sample taken from an individual asserting a particular origin and/or a particular time can be analyzed to determine one or more isotope ratios for the person. The isotope ratio may then be adjusted for a travel timing attested to by the person, and this adjusted ratio can be compared to the estimated ratio for a person in equilibrium with the attested point of origin. Alternatively, the adjusted ratio can be used to interrogate a map model of estimated body water ratios and thereby come up with a set of likely origins, depending on the estimated travel time.

The turnover model may utilize a traditional exponential fit approach based on an assumption that biological isotope exchange may be described by first-order rate kinetics. Alternatively, the turnover model may utilize a reaction-progress variable as described in Cerling et al., "Determining biological tissue turnover using stable isotopes: the reaction progress variable," *Oecologia* 151:175-189 (2007) and Podlesak et al., "Turnover of oxygen and hydrogen isotopes in the body water, CO2, hair, and enamel of a small mammal," *Geochimica et Cosmochimica Acta,* 72 (2008): 19-35, which are each incorporated by reference in their entireties.

Determining a travel history based upon an adjusted body water isotope ratio can further involve correlating the ratio with geographic information. This may be done by utilizing a model which correlates expected body water isotope ratios with likely geographic locations from which said ratios would arise. As discussed above, various sources serve as inputs that contribute to the body water isotope composition of each individual. Many of these inputs are environmental in nature, and therefore also vary with geography as do other environmental variables. Therefore, an important input layer to a geography-based body water isotope model can be provided by generating a map of the relevant input. While any potential isotopic inputs may be useful source layers for such a model, a more predictive model will be based on inputs that constitute larger contributions to body water composition and/or those that vary latitudinally and longitudinally. Two such inputs are drinking water and dietary inputs. Drinking water in particular is amenable to use for these purposes, because it is possible to sample drinking water sources, such as tap water, across an area and build a map of isotope ratios.

An exemplary approach according to this embodiment can include obtaining drinking water samples from a number of locations within a region, e.g., the United States, and determining the stable isotope ratios of those samples. Any non-randomness of this data set may be useful in instructing the model. For example, one may find a pattern in isotope ratios that correlates with geography. In a particular example one may find a pattern of spatial variation in isotope ratios based on latitude, longitude, elevation, location relative to bodies of water, or any combination of these. A detailed description of one such an analysis can be found in Bowen et al., "Stable isotope ratios of tap water in the contiguous Unites States," Water Resources Research, vol. 43, WO3419 (2007) which is incorporated herein by reference in it entirety.

Some temporal variation may also exist in isotope sources in addition to the geographic variation. Where present, this variation can be accounted for when modeling expected body water composition based on the isotope map. For example, one may collect water samples from various locations as described above and repeat the sampling on a regular basis (e.g. weekly, monthly, yearly). Any temporal variability may be used to further instruct a geographic isotope ratio model, so that the model can be more accurate regardless of the season in which it is used.

The data generated by sampling provides an empirical framework for a map of drinking water isotope ratios. However, for a fully predictive map it can be necessary to involve additional data set for purposes of interpolating geographic areas that have been sampled sparsely or not at all. For example, a rural region situated between two developed population centers may not have regular water supplies that are amenable to sampling. As such, overall patterns of variation in isotope data collected as described herein may be utilized for such interpolation. Additionally such variations can further be compared across elements, e.g. hydrogen and oxygen isotopes. For example, a strong correlation between tap water isotope ratios and predicted mean annual precipitation isotope ratios can reveal that local climatological water sources are the dominant control on tap water isotope ratios. This information can be used to determine which sources are more reliable for purposes of interpolation in the model. By then summing interpolated isotope ratios based on these sources with measured differences between tap water and such sources, a predictive map for measured isotopes can be generated.

Once equipped with an adjusted body water isotope ratio and a map model of relevant isotopic inputs, a further step in determining a travel origin for an individual can comprise transforming the adjusted body water isotope ratio to a value for the mapped isotope input. As discussed above, body water composition can be modeled as the product of a number of isotopic inputs and outputs, and relevant and predictive inputs are amenable to combination with spatial information. Accordingly, a model can be produced that estimates body water isotope ratios for individuals across geography. An exemplary embodiment includes a geographic information system (GIS) model that estimates the $\delta D$ and $\delta^{18}O$ of body water for humans across the United States. This model combines data layers such as the estimated $\delta D$ and $\delta^{18}O$ values for tap water and climatic data layers with the estimated $\delta$-values and molar fluxes (r) for all influxes and effluxes of oxygen and hydrogen to predict $\delta D_{bw}$ and $\delta^{18}O_{bw}$.

To model the isotopic composition of the body water, the isotopic composition and quantity of each input is known or estimated. Likewise, the quantity of each output and the fractionation between body water and each output is known or estimated. The following mass balance equations can be used to estimate $\delta_{bw}$. The isotopic enrichments are represented as the ratio (R). At steady state conditions, deuterium and $^{18}O$ of body water can be estimated for a one input and one output system using the following equation:

$$x_{in} \times R_{in} = x_{out} \times R_{out} \times \alpha_{bw} \qquad [4]$$

where x is the molar quantity of the input or output, R is the ratio of the heavy isotope to the light isotope and $\alpha_{bw}$ is the fractionation between body water and the output. Equation 4 can be expanded for multiple inputs and outputs and subsequently solved for $R_{bw}$.

$$R_{bw} = \frac{\sum_{i=1}^{n} x_{in,i} \times R_{in,i}}{\sum_{j=1}^{n} x_{out,j} \times \alpha_{out,j}} \quad [5]$$

For example, by inserting the specific inputs and outputs for deuterium in body water into the above equation:

$$R_{2Hbw} = \frac{(x_{dw}R_{dw} + x_{fw}R_{fw} + x_v R_v + x_{wvg}R_{wvg})}{(x_{bwl}\alpha_{bwl} + x_{tvl}\alpha_{tvl} + x_{rwl}\alpha_{rwl})} \quad [6]$$

and for $^{18}O$ in body water:

$$R_{18Obw} = \frac{(x_{dw}R_{dw} + x_{fw}R_{fw} + x_v R_v + x_{wvg}R_{wvg} + x_{O2}R_{O2})}{(x_{CO2}\alpha_{CO2} + x_{bwl}\alpha_{bwl} + x_{tvl}\alpha_{tvl} + x_{rwl}\alpha_{rwl})} \quad [7]$$

where x is the mole fraction of drinking water (dw), food water (fw), H or O bound in food (v), water vapor gain (wvg), diatomic O inspired from the atmosphere ($O_2$), breath water expelled (bwl), transcutaneous water loss (tvl), carbon dioxide expelled to the atmosphere ($CO_2$), and remaining water loss (rwl). Remaining water loss includes urine, fecal water and sweat. Remaining water may be assumed to be unfractionated relative to body water, whereas, transcutaneous water loss, carbon dioxide loss and breath water can be assumed to be related to body water by fractionation factors, $\alpha$.

The above equations can be parameterized for a human subject type of interest (e.g. adult or child; male or female) and then used to build a human body water model for such a subject. An example of this approach is described further in Example 2. Such equations can also be entered, together with information based on the geographic area of interest, into model building software to produce spatial models of the $\delta^2H$ and $\delta^{18}O$, or other relevant isotope ratios, of body water for the geographic area. This allows one to produce mechanistic models of these ratios for each pixel within a rasterized map of the geographic area.

Figure 5:
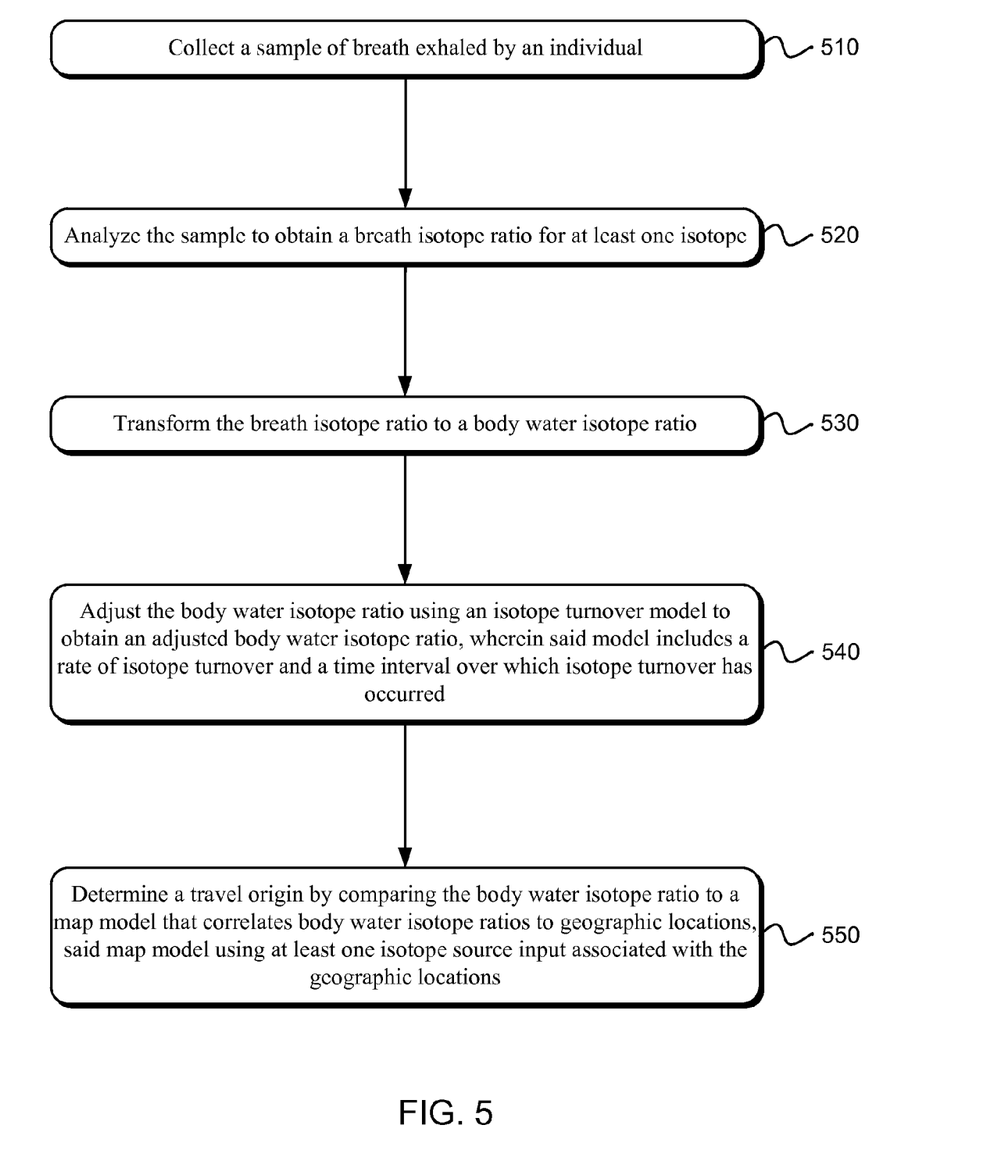
FIG. 5 is a flow diagram illustrating an example method for reconstructing a travel history for an individual.

FIG. 5 is a flow diagram illustrating an exemplary method for reconstructing a travel history for an individual. Beginning in block 510, a sample of breath exhaled by an individual can be collected. As in block 520, the sample can be analyzed to obtain a breath isotope ratio for at least one isotope. Then, as in block 530, the breath isotope ratio can be transformed to a body water isotope ratio. As in block 540, the body water isotope ratio can be adjusted using an isotope turnover model to obtain an adjusted body water isotope ratio. A model can be used that includes a rate of isotope turnover and a time interval over which isotope turnover has occurred. As in block 550, a travel origin can be determined by comparing the body water isotope ratio to a map model that correlates body water isotope ratios to geographic locations, said map model using at least one isotope source input associated with the geographic locations.

Figure 6:
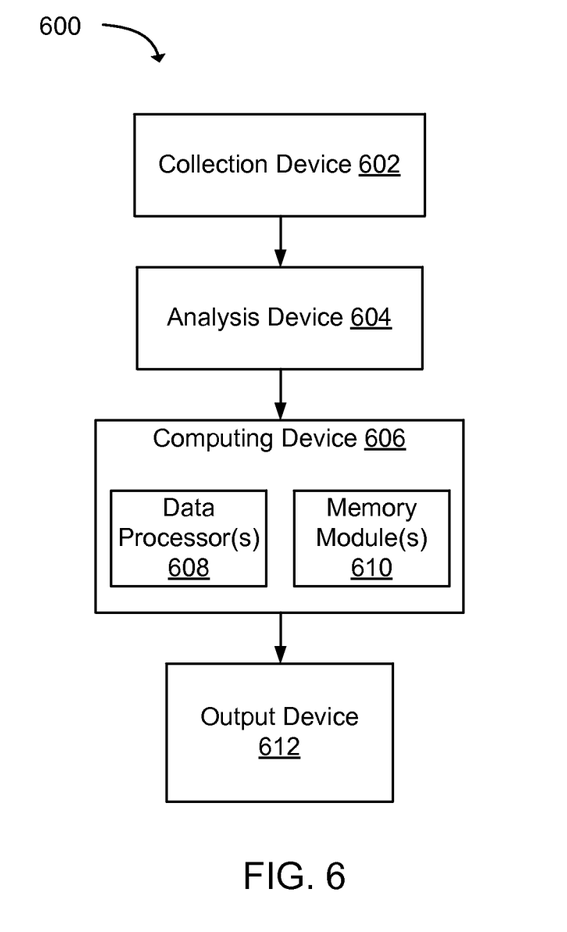
FIG. 6 is a block diagram that illustrates an example system for reconstructing a travel history for an individual.

FIG. 6 illustrates one embodiment of a system 600 for reconstructing a travel history for an individual. The system 600 can comprise a collection device 602 configured to collect a sample of breath exhaled by the individual. Such a collection device 602 may include or be based upon a conventional apparatus used for collecting breath samples. In a particular embodiment, the collection device 602 comprises a structure for collecting exhaled breath directly from the nose or mouth, e.g. a mask, nasal cannula, or mouthpiece. In an alternate embodiment, the collection device 602 may include an enclosed and sealed chamber into which the individual can enter. One or more samples may be then obtained from the air inside the chamber. Each sample of air can be analyzed isotopically and also analyzed for water concentration, some of which will come from the individual's breath. Contributions of isotopes from the surrounding air can be accounted for and negated by providing a control sample of the air prior to entry of the individual.

Accordingly, the system 600 can further include an analysis device 604 configured to accept the sample of breath and provide a measurement of a breath isotope ratio for at least one isotope. One approach to analysis is to inject the sample into a gas chromatography column coupled to a mass spectrometer. Another approach involves using a laser isotope analyzer, in which a laser beam is directed through a sample and the mixing ratio (or mole fraction) of a gas is determined from the measured absorption using Beer's Law, which may be expressed:

$$\frac{I_0}{I_v} = e^{-SL\chi P\phi_v} \quad [8]$$

where $I_v$ is the transmitted intensity through the sample at frequency v, $I_0$ is the (reference) laser intensity prior to entering the cell, P is the gas pressure, S is the absorption line strength of the probed transition, L is the optical path length, $\chi$ is the mixing ratio, and $\phi_v$ is the lineshape function of the transition at frequency v. In this case, $$\int \phi(v)dv = 1 \quad [9]$$

This technique has proven successful in determining gas compositions, even in samples containing several species of gas, without the need for reference standards or calibration gases. Accordingly, in a particular embodiment of the present invention, the isotope composition of the breath is analyzed by laser absorption spectroscopy. The laser can in turn be coupled to a computer for interpretation of results. One commercial example of a suitable laser spectroscopy device is a water-vapor isotope analyzer available from Los Gatos Research, although other such devices can be suitable.

The system can further comprise a computing device 606 that includes one or more memory module(s) 610 and one or more a data processor(s) 608 configured to accept the measurements from the analysis device 604, either by direct wired connection or remotely by radio or other wireless connection. The data processor 608 may be further configured to input the isotope measurement into one or more of the models described herein, and to perform transformations to the data that facilitate use of the model. In a particular embodiment, the data processor 608 includes a computer onto which is loaded one or more programs. The programs may include code that embodies one or more of the isotope ratio models described herein. In addition, one or more of the programs may include routines for adjusting or transforming isotope measurements for use in the models. The calculated travel origin can then be communicated, e.g. visually or audibly, so that the travel history can be verified or otherwise assessed.

An output device 612, such as a graphical display and/or speaker can readily serve this display function.

Figure 7:
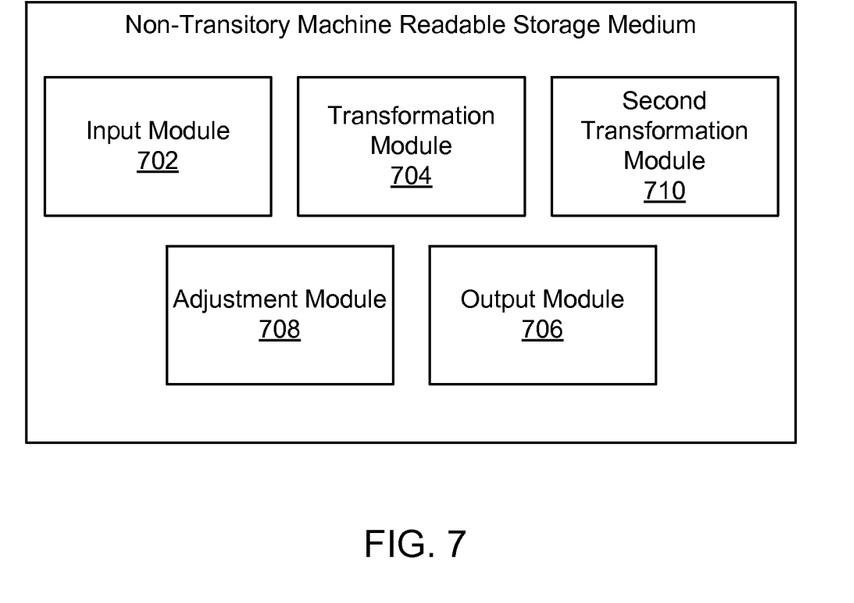
FIG. 7 is a block diagram illustrating an example of a machine readable storage medium that includes a plurality of executable modules.

FIG. 7 illustrates an example of a non-transitory machine readable storage medium having instructions embodied thereon where the instructions are executable by a processor to determine a travel origin for an individual. In one embodiment, the machine readable storage can contain an input module 702, a transformation module 704, a second transformation module 710, an adjustment module 708 and an output module 706. The input module 702 can receive isotope ratio data in the form of breath isotope ratio measurements and a time interval. The transformation module 704 can transform the isotope ratio data received from the input module 702 into body water isotope ratios, where the transformation module 704 may include a body water model correlating breath isotope ratio measurements to body water isotope ratios. The second transformation module 710 can transform the body water isotope ratio to at least one input isotope ratio. The adjustment module 708 can calculate an adjusted body water isotope ratio based on isotope turnover during the time interval, where the adjustment module 708 can include an isotope turnover model including a rate of isotope turnover. The output module 706 can compare the body water isotope ratio received from the transformation module 704 to a map model correlating body water isotope ratios to geographical locations, and output the travel origin to an output device.

Optionally, statistical confidence intervals regarding a calculated travel history can be correlated based on the degree of corresponding data and interpolation given a particular set of sampled isotope ratios from the individual. Similarly, one or more predicted travel origins may be displayed which have a statistical significance in order to provide information on which to judge accuracy of assertions made by an individual regarding their travel history.

EXAMPLES

The following examples illustrate various embodiments of the invention. Thus, these examples should not be considered as limitations of the present invention, but are merely in place to teach how to implement the present invention based upon current experimental data.

Example 1

Building a Geographic Model of Isotope Ratios

Five hundred and ten tap water samples for spatial characterization were obtained from 496 towns and cities within the contiguous United States. Samples were obtained from each of the 48 contiguous States, with few sampling gaps greater than ~100 km in radius. Notable exceptions include sparse sampling in eastern Oregon, central Nevada, central Texas, and eastern Montana. The stable isotope ratios of these samples span a large range of values from −152 to +11‰ ($\delta^2H$) and −19.4 to +4.2‰ ($\delta^{18}O$). Average values for the sample set are −66‰ for $\delta^2H$ and −8.9‰ for $\delta^{18}O$. For each element the data distribution is somewhat bimodal, with a dominant mode similar to the lumped average and a minor mode near −118‰ ($\delta^2H$) and −16‰ ($\delta^{18}O$). The tap water data cluster near the Global Meteoric Water Line ($\delta^2H = \delta^{18}O \times 8 + 10$) characterizing average global precipitation, but many samples lie below this line. Deuterium excess (d, $d = \delta^2H - \delta^{18}O \times 8$) values for the sample set range from −22.2 to 22.4‰, with an average value of 5.5‰.

Figure 3:
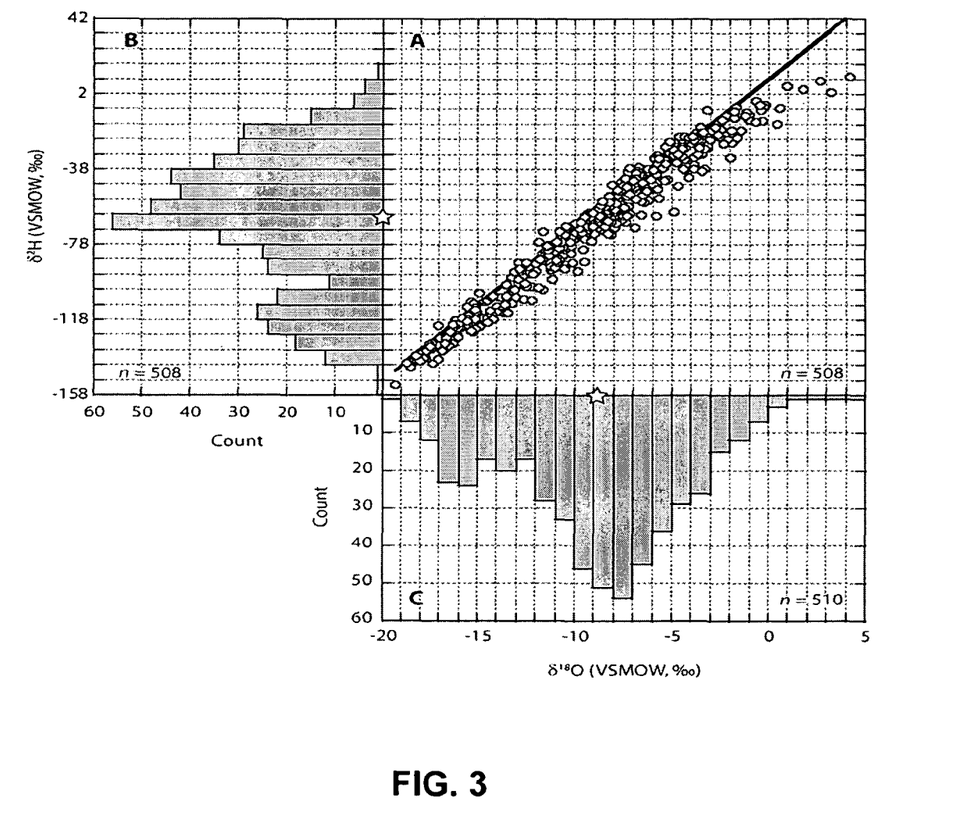
FIG. 3 is a graph of stable H- and O-isotope ratios for spatial data set tap water samples. Covariation of $\delta^2 H$ and $\delta^{18}O$ values are in Sector A of the graph. The bold black line represents the Global Meteoric Water Line. Frequency distributions for the individual isotope ratios are in Sectors B and C of the graph. White stars show the mean values for each isotope ratio for the entire data set.

The spatial distribution of tap water stable isotope ratios is non-random (Moran's I=0.68 and 0.59, Z=7.9 and 6.8, $p<0.01$ for $\delta^2H$ and $\delta^{18}O$, respectively). The lowest $\delta^2H$ and $\delta^{18}O$ values (<−110‰ and <−14‰, respectively) occur throughout the northern Rocky Mountain States (primarily Idaho, Montana, Utah, and Wyoming), and samples from this region comprise the lower, minor mode of the hydrogen and oxygen isotope ratio distributions shown in FIG. 3. The highest $\delta^2H$ and $\delta^{18}O$ values for USA tap water samples (>0‰ for each element) represent samples from a relatively restricted region of north-central Texas and south-central Oklahoma. Other samples with relatively high values were obtained throughout the Gulf Coast States. The general pattern of spatial variation for isotope ratios of each element is one of decreasing values from low-latitude, low-elevation coastal regions towards inland, high-latitude, and mountainous areas. In contrast to the H and O isotope ratio values, d values for the USA tap water samples show no clear, overarching spatial pattern in their distribution, and values of d between 5 and 10‰ occur throughout the contiguous United States. Extreme values of d, however, appear to be limited to certain regions, with the highest d values (>16‰) found in the northeastern USA (e.g., New England) and the lowest (<−10‰) concentrated in southern California and along the lower Colorado River, along the Missouri River, and in north-central Texas and south-central Oklahoma.

Example 2

Measuring Temporal Variation in Isotope Ratios Across Geographic Regions

Five hundred and sixty-eight water samples were collected across the U.S. and analyzed as a part of a monthly water survey effort. The average isotope ratios and interannual variability are shown in Table 1. The spatial density of the monthly water survey sampling sites was much lower than that of the spatial characterization sampling sites in Example 1, but the distribution of these sites still encompassed much of the physiographic and climatological variation present in the lower 48 States.

TABLE 1

Average isotope ratios and interannual variability for monthly tap water survey.

| | | | Average | | 1σ | |
|---|---|---|---|---|---|---|
| City | State/Province | N | $\delta^2H$ | $\delta^{18}O$ | $\delta^2H$ | $\delta^{18}O$ |
| Lethbridge | Alberta | 13 | −135 | −17.3 | 4 | 0.6 |
| Tempe | AZ | 11 | −75 | −9.4 | 6 | 0.7 |
| Tucson | AZ | 10 | −62 | −8.3 | 2 | 0.1 |
| Tucson | AZ | 12 | −62 | −8.2 | 2 | 0.2 |
| Berkeley | CA | 12 | −83 | −11.4 | 9 | 1.3 |
| Buena Park | CA | 10 | −71 | −9.2 | 9 | 0.8 |
| Davis | CA | 11 | −56 | −8.0 | 2 | 0.2 |
| Davis | CA | 11 | −52 | −7.4 | 3 | 0.3 |
| Fullerston | CA | 12 | −77 | −9.7 | 2 | 0.2 |
| Pasadena | CA | 12 | −65 | −8.5 | 8 | 0.8 |
| San Diego | CA | 11 | −78 | −9.5 | 4 | 0.5 |
| San Diego | CA | 11 | −78 | −9.5 | 6 | 0.7 |
| Boulder | CO | 14 | −116 | −15.4 | 5 | 1.1 |
| Coral Gables | FL | 8 | −4 | −0.8 | 1 | 0.1 |
| Tallahassee | FL | 13 | −11 | −1.8 | 2 | 0.2 |
| Tallahassee | FL | 10 | −16 | −2.8 | 2 | 0.1 |
| Tallahassee | FL | 10 | −16 | −2.9 | 3 | 0.2 |
| Athens | GA | 13 | −25 | −4.3 | 2 | 0.3 |
| Watkinsville | GA | 12 | −28 | −5.2 | 2 | 0.2 |
| Boise | ID | 12 | −129 | −16.8 | 3 | 0.3 |
| Chicago | IL | 9 | −44 | −5.8 | 2 | 0.2 |
| Westmont | IL | 9 | −45 | −5.8 | 2 | 0.2 |
| Evansville | IN | 12 | −50 | −7.5 | 5 | 1.0 |

TABLE 1-continued

Average isotope ratios and interannual variability for monthly tap water survey.

| City | State/Province | N | Average $\delta^2H$ | Average $\delta^{18}O$ | 1σ $\delta^2H$ | 1σ $\delta^{18}O$ |
|---|---|---|---|---|---|---|
| Lawrence | KS | 13 | −28 | −4.0 | 7 | 1.0 |
| Manhattan | KS | 12 | −37 | −5.4 | 2 | 0.4 |
| Rockville | MD | 12 | −49 | −7.5 | 3 | 0.4 |
| Minneapolis | MN | 11 | −58 | −7.5 | 9 | 1.1 |
| Minneapolis | MN | 12 | −57 | −7.4 | 10 | 1.2 |
| Wykoff | MN | 13 | −63 | −9.3 | 2 | 0.4 |
| Durham | NH | 11 | −56 | −8.5 | 5 | 0.9 |
| Albuquerque | NM | 13 | −97 | −13.0 | 1 | 0.3 |
| Las Vegas | NV | 13 | −97 | −11.8 | 1 | 0.3 |
| Reno | NV | 13 | −110 | −14.7 | 1 | 0.1 |
| Reno | NV | 12 | −89 | −11.5 | 9 | 1.7 |
| Ithaca | NY | 13 | −71 | −10.3 | 8 | 1.2 |
| Columbus | OH | 10 | −54 | −8.0 | 7 | 1.3 |
| Eugene | OR | 12 | −75 | −10.4 | 2 | 0.2 |
| Eugene | OR | 12 | −83 | −11.7 | 3 | 0.3 |
| Portland | OR | 13 | −69 | −9.9 | 4 | 0.5 |
| University Park | PA | 13 | −60 | −9.2 | 1 | 0.2 |
| Austin | TX | 11 | −17 | −2.4 | 1 | 0.2 |
| Dallas | TX | 11 | −4 | −0.3 | 6 | 1.1 |
| Houston | TX | 13 | −12 | −2.1 | 4 | 0.9 |
| Houston | TX | 13 | −13 | −2.2 | 5 | 1.0 |
| Salt Lake City | UT | 12 | −120 | −15.9 | 2 | 0.3 |
| Great Falls | VA | 12 | −47 | −7.8 | 1 | 0.1 |
| Herndon | VA | 8 | −46 | −7.3 | 4 | 0.6 |

The isotope ratios of tap water from the monthly sample set range from −144 to +4‰ for $\delta^2H$ (average=−61‰) and from −18.9‰ to +1.2‰ for $\delta^{18}O$ (average=−8.4‰). Annual average $\delta^2H$ and $\delta^{18}O$ values for the monthly sampling locations (calculated as unweighted averages of the monthly samples) range from −135‰ to −4‰ (average=−60‰) and from −17.3‰ to −0.5‰ (average=−8.2‰), respectively. Tests of the mean and variance of these distributions suggest that the distribution of monthly survey $\delta^2H$ and $\delta^{18}O$ values is not statistically different than that of the spatial characterization data set (F-test for variance, p=0.49 and 0.51; T-test for means, p=0.28 and 0.33 for $\delta^2H$ and $\delta^{18}O$, respectively). Intra-annual variation in tap water isotope ratios was calculated as the standard deviation of isotope ratios for the monthly samples, and ranges from 1 to 10‰ for $\delta^2H$ and from 0.1 to 1.7‰ for $\delta^{18}O$. The average 1σ value across all sites is 4‰ and 0.6‰ for $\delta^2H$ and $\delta^{18}O$, respectively, or ~2.3% of the range of values measured in the spatial characterization survey for each element. Inter-annual variation (1σ) in tap water d values ranges from 0.9 to 5.4‰, with an average value of 2.2‰, or approximately 5% of the total range observed for all tap water samples.

Example 3

Building a Human Body Water Isotope Model

A working example of a model in accordance with an embodiment of the invention is presented below, based on an adult male and an adult female, each on an average American diet. There were four spatial models of the $\delta^2H_{bw}$ and $\delta^{18}O_{bw}$ for the contiguous United States. The first was for an adult male (V_1), the second for and adult female (V_2), the third for and adult male with the $\delta^2H$ and $\delta^{18}O$ values of food held constant (V_3), and the fourth for an adult male that drank local precipitation instead of local tap water (V_4). The following series of equations are used to estimate the molar quantities and fractionation factors that are subsequently input into equations [6] and [7] to estimate $\delta^2H_{bw}$ and $\delta^{18}O_{bw}$ for humans.

Determining the Molar Quantities of Inputs

First the Harris-Benedict equations were used to determine a daily total energy expenditure ($P_j$) for adult males (j=1) and females (j=2):

$$P_j = (c_{1,j} + c_{2,j} m_b + c_{3,j} h - c_{4,j} Y) A c_5 \quad [10]$$

where $m_b$ is the mass, h is the height, Y is the age and A is the activity level of the individual. Tables 1 and 2 show values and descriptions for all variables and constants used in equations 8 through 25.

TABLE 2

Quantity, symbol, unit, values and literature source used in the 4 parameterizations (V_1[1], V_2[2], V_3[3], V_4[4]) of the body water model.

| Quantity | Symbol | Unit | V_1 | V_2 | V_3 | V_4 |
|---|---|---|---|---|---|---|
| Mass | $m_b$ | kg | 83 | 75 | 83 | 83 |
| Height | h | cm | 180 | 164 | 180 | 180 |
| Total energy expenditure | $P_j$ | kj d$^{-1}$ | Eq. 10 | Eq. 10 | Eq. 10 | Eq. 10 |
| Age | Y | a | 40 | 40 | 40 | 40 |
| Activity level | A | | 1.6 | 1.6 | 1.6 | 1.6 |
| Mass of food | $m_f$ | kg | Eq. 11 | Eq. 11 | Eq. 11 | Eq. 11 |
| Extraction efficiency | φ | | 1 | 1 | 1 | 1 |
| Digestibility | γ | | 0.85 | 0.85 | 0.85 | 0.85 |
| Fraction carbohydrate in diet | $w_c$ | | 0.53 | 0.53 | 0.53 | 0.53 |
| Fraction fat in diet | $w_f$ | | 0.32 | 0.32 | 0.32 | 0.32 |
| Fraction protein in diet | $w_p$ | | 0.15 | 0.15 | 0.15 | 0.15 |
| Amount of H and O in food | $m_v$ | mol | Eq. 12 | Eq. 12 | Eq. 12 | Eq. 12 |
| Amount of diatomic oxygen | $m_{O2}$ | mol | Eq. 13 | Eq. 13 | Eq. 13 | Eq. 13 |
| Amount of water in food | $m_{fw}$ | mol | Eq. 14 | Eq. 14 | Eq. 14 | Eq. 14 |
| Fraction water content in food | $w_{cf}$ | | 0.65 | 0.65 | 0.65 | 0.65 |
| Air flow through lungs | $o_{air}$ | l mol$^{-1}$ | Eq. 15 | Eq. 15 | Eq. 15 | Eq. 15 |
| Amount of H and O gain in lungs | $m_{wvg}$ | mol | Eq. 16 | Eq. 16 | Eq. 16 | Eq. 16 |
| Ambient relative humidity | $H_a$ | | MRH | MRH | MRH | MRH |
| Lung relative humidity | $H_l$ | | 1.0 | 1.0 | 1.0 | 1.0 |
| Ambient temperature | $t_a$ | °C. | MAT | MAT | MAT | MAT |
| Ambient thermodynamic temperature | $T_k$ | K | convert | convert | convert | convert |
| Lung temperature | $t_l$ | °C. | 33 | 33 | 33 | 33 |
| Amount of H and O in drinking water | $m_{dw}$ | mol | Eq. 17 | Eq. 17 | Eq. 17 | Eq. 17 |
| Total amount of flow of H and O | $m_{WFj}$ | mol | 211.11 | 183.3 | 211.11 | 211.11 |
| Amount of O lost in $CO_2$ | $m_{CO2}$ | mol | Eq. 18 | Eq. 18 | Eq. 18 | Eq. 18 |

TABLE 2-continued

Quantity, symbol, unit, values and literature source used in the 4 parameterizations
($V\_1^1, V\_2^2, V\_3^3, V\_4^4$) of the body water model.

| Quantity | Symbol | Unit | V_1 | V_2 | V_3 | V_4 |
|---|---|---|---|---|---|---|
| Surface area | S | $m^2$ | Eq. 19 | Eq. 19 | Eq. 19 | Eq. 19 |
| Amount of H and O lost | $m_{tvl}$ | mol | Eq. 20 | Eq. 20 | Eq. 20 | Eq. 20 |
| Amount of H and O lost through | $m_{bwl}$ | mol | Eq. 21 | Eq. 21 | Eq. 21 | Eq. 21 |
| Amount of remaining H and O lost | $m_{rwl}$ | mol | Eq. 22 | Eq. 22 | Eq. 22 | Eq.22 |
| $\delta^{18}O$ diatomic oxygen | $\delta^{18}O_{O2}$ | ‰ | 15.3 | 15.3 | 15.3 | 15.3 |
| $\delta^2$ drinking water | $\delta^2 H_{dw}$ | ‰ | Tap[5] | Tap[5] | Tap[5] | Precip.[6] |
| $\delta^{18}O$ drinking water | $\delta^{18}O_{dw}$ | ‰ | Tap[5] | Tap[5] | Tap[5] | Precip.[6] |
| $\delta^2 H$ food | $\delta^2 H_{fd}$ | ‰ | Eq. 23 | Eq. 23 | −115 | Eq. 23 |
| $\delta^{18}O$ food | $\delta^{18}O_{fd}$ | ‰ | Eq. 23 | Eq. 23 | 32 | Eq. 23 |
| $\delta^2$ food water | $\delta^2 H_{fw}$ | ‰ | Eq. 24 | Eq. 24 | Eq. 24 | Eq. 24 |
| $\delta^{18}O$ food water | $\delta^{18}O_{fw}$ | ‰ | Eq. 25 | Eq. 25 | Eq. 25 | Eq. 25 |

[1] V_1: Model for an adult male created using estimated δ-values of tap water
[2] V_2: Model for an adult female created using estimated δ-values of tap water
[3] V_3: Model for an adult male created using estimated δ-values of tap water and the δ-values of food held constant
[4] V_4: Model for an adult male created using estimated δ-values of precipitation
[5] Tap represents $\delta^{18}O$ and $\delta^2 H$ values of local tap water.
[6] Precip. Represents estimated $\delta^2 H$ and $\delta^{18}O$ values of local precipitation.

TABLE 3

Equation number, value, unit of measure, and source
of constants used to predict $\delta^2 H_{bw}$ and $\delta^{18}O_{bw}$ values in body
water models $V\_1^1, V\_2^2, V\_3^3$, and $V\_4^4$.

| Equation | Constants | Value | Unit |
|---|---|---|---|
| Eq. 10 | $c_{1,1}$ | 66 | |
| Eq. 10 | $c_{2,1}$ | 13.8 | |
| Eq. 10 | $c_{3,1}$ | 5.0 | |
| Eq. 10 | $c_{4,1}$ | 6.8 | |
| Eq. 10 | $c_5$ | 4.1868 | |
| Eq. 10 | $c_{1,2}$ | 655 | |
| Eq. 10 | $c_{2,2}$ | 9.6 | |
| Eq. 10 | $c_{3,2}$ | 1.9 | |
| Eq. 10 | $c_{4,2}$ | 4.7 | |
| Eq. 11 | $k_1$ | 17.3 | kJ $kg^{-1}$ |
| Eq. 11 | $k_2$ | 39.7 | kJ $kg^{-1}$ |
| Eq. 11 | $k_3$ | 20.1 | kJ $kg^{-1}$ |
| Eq. 12 | $f_{1,1}$ | 30.9 | mol $kg^{-1}$ |
| Eq. 12 | $f_{2,1}$ | 60.0 | mol $kg^{-1}$ |
| Eq. 12 | $f_{3,1}$ | 11.0 | mol $kg^{-1}$ |
| Eq. 12 | $f_{1,2}$ | 15.4 | mol $kg^{-1}$ |
| Eq. 12 | $f_{2,2}$ | 2.0 | mol $kg^{-1}$ |
| Eq. 12 | $f_{3,2}$ | 3.0 | mol $kg^{-1}$ |
| Eq. 13 | $k_4$ | 0.00216 | mol O2 $kJ^{-1}$ |
| Eq. 14 | $k_5$ | 55.56 | mol $kg^{-1}$ |
| Eq. 15 | $k_6$ | 22.4 | l $mol^{-1}$ |
| Eq. 15 | $k_7$ | 0.20 | % efficiency lungs |
| Eq. 15 | $k_8$ | 0.21 | % $O_2$ in atm. |
| Eq. 16 and 21 | $k_9$ | 10 | |
| Eq. 16 and 21 | $k_{10}$ | 0.686 | |
| Eq. 16 and 21 | $k_{11}$ | 0.027 | |
| Eq. 16 and 21 | $k_{12}$ | 760 | |
| Eq. 18 | $k_{13}$ | 2.0 | |
| Eq. 19 | $k_{14}$ | 3600 | |
| Eq. 20 | $k_{15}$ | 0.14 | g $min^{-1} m^{-2}$ |
| Eq. 20 | $k_{16}$ | 18 | moles $g^{-1}$ |
| Eq. 23 | $a_{1,1}$ | −30[5] | ‰ |
| Eq. 23 | $a_{2,1}$ | −167[5] | ‰ |
| Eq. 23 | $a_{3,1}$ | −33[5] | ‰ |
| Eq. 23 | $a_{1,2}$ | 27[5] | ‰ |
| Eq. 23 | $a_{2,2}$ | 22[5] | ‰ |
| Eq. 23 | $a_{3,2}$ | 33[5] | ‰ |
| Eq. 24 | $k_{17}$ | 0.69 | |
| Eq. 24 | $k_{18}$ | 3.8 | ‰ |
| Eq. 25 | $k_{19}$ | 4.0 | ‰ |
| Eq. 26 | $k_{20}$ | 1158.8 | |
| Eq. 26 and 27 | $k_{21}$ | $10^9$ | |
| Eq. 26 | $k_{22}$ | 1620.1 | |
| Eq. 26 and 27 | $k_{23}$ | $10^6$ | |
| Eq. 26 | $k_{24}$ | 794.84 | |
| Eq. 26 and 27 | $k_{25}$ | $10^3$ | |
| Eq. 26 | $k_{26}$ | 161.04 | |
| Eq. 26 | $k_{27}$ | 2.9992 | |
| Eq. 27 | $k_{28}$ | −7.685 | |
| Eq. 27 | $k_{29}$ | 6.7123 | |
| Eq. 27 | $k_{30}$ | 1.6664 | |
| Eq. 27 | $k_{31}$ | 0.35041 | |
| Hydrogen α values | $\alpha_{Hwater-vapor}$ | Variable | |
| | $\alpha_{Htvl-bw}$ | 0.935 | |
| | $\alpha_{Hbwl-bw}$ | 0.946 | |
| Oxygen α values | $\alpha_{Owater-vapor}$ | Variable | |
| | $\alpha_{Otvl-bw}$ | 0.981 | |
| | $\alpha_{Obwl-bw}$ | 0.991 | |
| | $\alpha_{OCO2-bw}$ | 1.038 | |

[1] V_1: Model for an adult male created using estimated δ-values of tap water
[2] V_2: Model for an adult female created using estimated δ-values of tap water
[3] V_3: Model for an adult male created using estimated δ-values of tap water and the δ-values of food held constant
[4] V_4: Model for an adult male created using estimated δ-values of precipitation
[5] These values can be modified to increase fit of model to measured values.

The amount of food consumed ($m_f$) by the individual to fuel $P_j$ was calculated as:

$$m_f = P_j / [\phi\gamma(k_1 w_c + k_2 w_f + k_3 w_p)] \quad [11]$$

where $\phi$ is the extraction efficiency, $\gamma$ is the digestibility of the diet, $w_c$ is the fraction of carbohydrate in the diet, $w_f$ is the fraction of fat in the diet and $w_p$ is the fraction of protein in the diet ($w_c + w_1 + w_p = 1$).

Next the amount of H(q=1) and O(q=2) in the mass of food consumed ($m_{v,q}$) were calculated as:

$$m_{v,q} = m_f \phi\gamma(f_{1,q} w_c + f_{2,q} w_1 + f_{3,q} w_p) \quad [12]$$

Then the amount of $O_2$ ($m_{O2}$) required to fuel the estimated $P_j$:

$$m_{O2} = k_4 P_j \quad [13]$$

The amount of food water in the mass of food consumed was determined as:

$$m_{fw} = k_5 m_f W_{cf} / (1 - W_{cf}) \quad [14]$$

where $W_{cf}$ is the fraction of water in food.

The air flow through the lungs ($o_{air}$) was calculated as $$o_{air} = k_6 m_{O2} / (k_7 k_8) \quad [15]$$

The amount of water gain ($m_{wvg}$) across the lungs was determined as $$m_{wvg} = [H_a k_9^{(k_{10}+k_{11}t_a)} o_{air}]/(k_{12} k_6) \quad [16]$$

where $H_a$ is the ambient relative humidity and $t_a$ is the ambient temperature. Values of 58% for $H_a$ and 17.6° C. for $t_a$ were used to develop the model.

The amount of drinking water ($m_{dw}$) necessary to balance the daily water budget by using the total water flow ($m_{WFj}$) for an individual was calculated as $$m_{dw} = m_{WFj} - m_{wvg} - m_{v,1} - m_{fw} \quad [17]$$

A mean total water flow for an adult male of 3.8 L/day and 3.3 L/day for an adult female were used.

Determining the Molar Quantities of Outputs

In the next steps the molar quantities of all outputs of hydrogen and oxygen were calculated. First, the moles of oxygen lost as carbon dioxide ($m_{CO2}$) as $$m_{CO2} = m_{O2} - m_{v,1}/k_{13} - m_{v,2} \quad [18]$$

Next, the moles of water lost as transcutaneous water vapor (twv), calculated by using the Dubois formula to calculate the surface area (BSA) for the individual $$S = \sqrt{h m_b/k_{14}} \quad [19]$$

and using the following equation to calculate $m_{tvl}$ as $$m_{tvl} = k_{15} S/k_{16} \quad [20]$$

It has been determined that humans lose 0.14 g/min/m² through their skin and it can be assumed that clothing decreases the amount of water lost by 50%. The amount of water lost per minute was converted to a daily water loss.

The moles of water lost through breathing ($m_{bwl}$) were determined as $$m_{bwl} = [H_1 k_9^{(k_{10}+k_{11}t_1)} o_{air}]/(k_{12} k_6) \quad [21]$$

where $h_1$ is the relative humidity in the lungs (100%) and $t_1$ is the temperature in the lungs (33° C.). Lastly, the water lost as urine, sweat and in the feces were calculated. In all calculations, these three outputs are referred to as remaining water loss ($m_{rwl}$):

$$m_{rwl} = m_{WFj} - m_{tvl} - m_{bwl} \quad [22]$$

Estimating the Isotopic Composition and Fractionation Factors for all Inputs

The isotopic composition and the fractionation factors of all inputs of hydrogen and oxygen were then estimated. One assumption made was that the $\delta^{18}O$ of oxygen absorbed in the lungs was 15.3‰. Next, in estimating the $\delta^{18}O$ and $\delta^2H$ of food consumed, two parameterizations were used, one in which the $\delta^2H$ and $\delta^{18}O$ of food was linked by equations 24 and 25 to the $\delta^2H_{dw}$ and $\delta^{18}O_{dw}$ values, respectively. Much of the food consumed in the United States is not of a local origin and to determine the importance of food to estimated δ-values of body water, $\delta^2H_{bw}$ and $\delta^{18}O_{bw}$ were calculated using static values of food based on previously measured values: $\delta^2H$ of food of −115‰ and a value of 32‰ for the $\delta^{18}O$ of food. Food ($\delta^{18}O_{fd}$):

$$\delta_{fd,q} = [f_{1,q} w_c m_f p \gamma/m_{v,q})(\delta_{dw,q} + a_{1,q})] + [f_{2,q} w_1 m_f p \gamma/m_{v,q}) \\ (\delta_{dw,q} + a_{2,q})] + [f_{3,q} w_p m_f p \gamma/m_{v,q})(\delta_{dw,q} + a_{3,q})] \quad [23]$$

Food Water ($\delta^{18}O_{fw}$):

$$\delta^{18}O_{fw} = \delta^{18}O_{dw} + 4 \quad [24]$$

$$\delta^2H_{fw} = 0.69 * \delta^2H_{dw} + 3.75 \quad [25]$$

Next, convert the above estimated $\delta^{18}O$ and $\delta^2H$ values into R values. The R value for the water vapor gain (wvg) may be estimated using the following equations for each element:

H: $R_{Hwvg} = R_{Hdw}/[\text{Exp}((k_{20}T_k^3/k_{21} - k_{22}T_k^2/k_{23} + k_{24}T_k/k_{25} - k_{26} + k_{27}k_{21}/T_k^3)/k_{25})]$ [26]

O: $R_{Owvg} = R_{Odw}/[\text{Exp}((k_{28} + k_{29}k_{25}/T_k - k_{30}k_{23}/T_k^2 + k_{31}k_{21}/T_k^3)/k_{25})]$ [27]

where $T_k$ = temperature in Kelvin.

Estimating the Isotopic Composition and Fractionation Factors for all Outputs

Lastly, the isotopic composition and fractionation factors for all outputs were estimated. The empirically derived estimate for the equilibrium fractionation ($\alpha_{CO2-bw} = 1.038$) between $\delta^{18}O_{bw}$ and $\delta^{18}O$ value of $CO_2$ was used. The fractionation factors (H: $\alpha_{Htvl-bw} = 0.935$; O: $\alpha_{Otvl-bw} = 0.981$) were used for the fractionation between body water and water lost transcutaneously) and H: $\alpha = 0.946$; O; $\alpha$ of 0.991 for the fractionation between body water and water lost through breathing. Urine, sweat and fecal water were assumed to be unfractionated relative to body water. The molar quantities, R values and α values for all inputs and outputs are inserted into equations [6] and [7] to produce estimates of $\delta^2H_{bw}$ and $\delta^{18}O_{bw}$.

Example 4

Steady-State Body Water Model Projections

Figure 4:
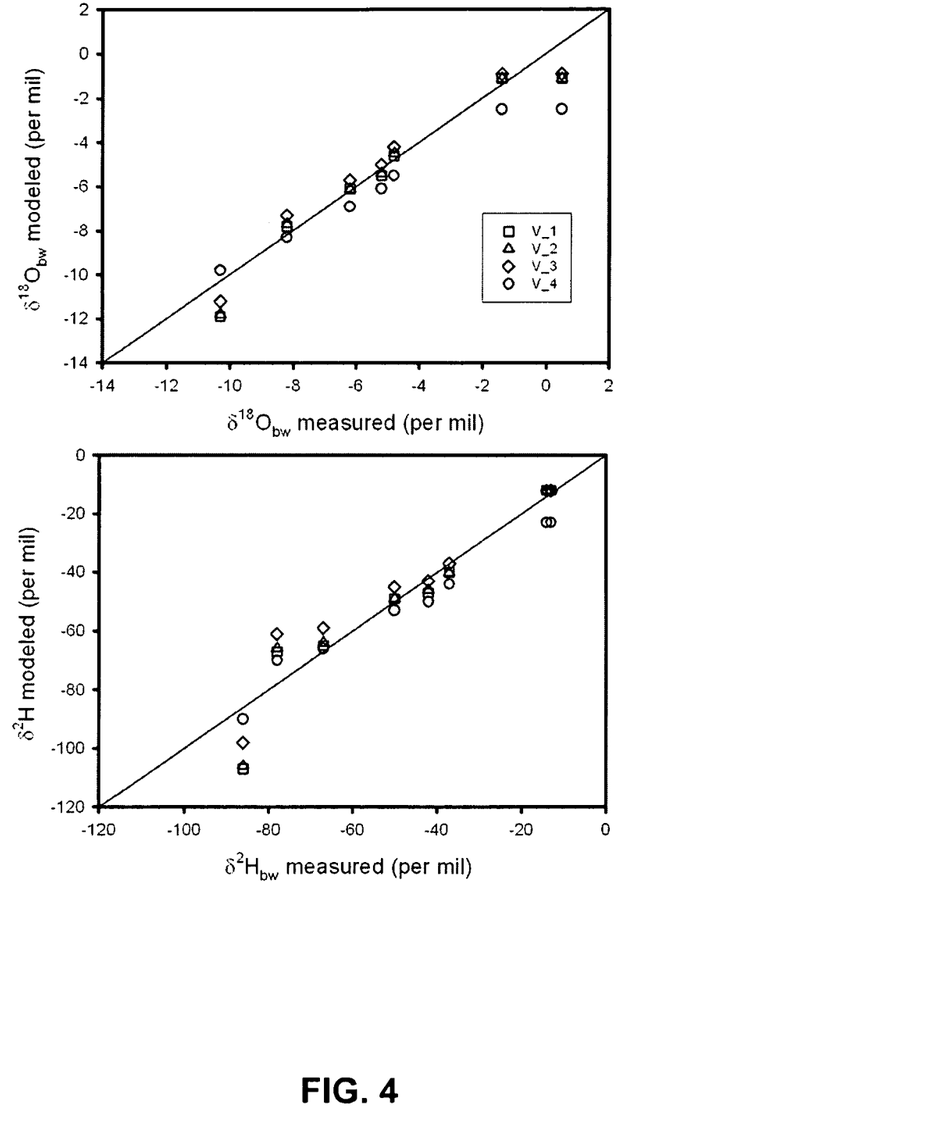
FIG. 4 shows A) comparison between estimated $\delta^{18}O_{bw}$ with measured $\delta^{18}O_{bw}$ values from the literature; B) comparison between estimated $\delta^2 H_{bw}$ with measured $\delta^2 H_{bw}$ values collected from the literature.

We created four spatial models of the $\delta^2H_{bw}$ and $\delta^{18}O_{bw}$ for the contiguous United States. The predicted values for males (V__1), for females (V__2) and for males with the $\delta^2H$ and $\delta^{18}O$ values of food held constant (V__3) were similar and when the modeled values were regressed against the measured values, the slope of the lines were indistinguishable from 1 for all three models (Table 4; FIG. 4). The model with the greatest difference between modeled and measured values was the model in which predicted $\delta^2H$ and $\delta^{18}O$ values of precipitation were used for drinking water (V__4). The slope of the relationship between measured and modeled values was significantly less than 1 (Table 4; FIG. 4).

The spatial model in which the $\delta^2H$ and $\delta^{18}O$ values of food were linked to local drinking water for an adult male (V__1) estimated that $\delta^2H_{bw}$ and $\delta^{18}O_{bw}$ values ranged from 4‰ to −147‰ for hydrogen and 1.4 to −16.3 for oxygen across the contiguous United States. The most enriched $\delta^2H_{bw}$ and $\delta^{18}O_{bw}$ values were in interior Texas and along the Gulf Coast and the most depleted values were in the higher latitudes and elevations of the interior West. Estimated values for all locations, except for Mt. Rainer, were within 10‰ for hydrogen and 0.7‰ for oxygen of published values (Table 4). When the $\delta^2H_{bw}$ and $\delta^{18}O_{bw}$ estimated using V__1 model were compared to $\delta^2H$ and $\delta^{18}O$ values of local drinking water, the largest differences were in the interior West. The differences between estimated $\delta^2H_{bw}$ and $\delta^{18}O_{bw}$ values and $\delta^2H$ and $\delta^{18}O$ values of drinking water ranged from 3‰ to 18‰ for hydrogen and from 0.4‰ to 5.3‰ for oxygen.

Overall, models V__1 for men and V__2 for women closely matched measured $\delta^2H_{bw}$ and $\delta^{18}O_{bw}$ values from the literature (Table 4). For example, the body water model estimates were within ±10‰ for hydrogen and within ±0.7‰ for oxygen for all locations except for the samples from Mt. Rainer. The largest differences between measured and modeled $\delta^2H_{bw}$ and $\delta^{18}O_{bw}$ values was for the model in which estimated $\delta^2H$ and $\delta^{18}O$ values of precipitation were used as the values for drinking water (V__4). Estimated $\delta^2H_{bw}$ and $\delta^{18}O_{bw}$ values from model V__1 differed by a magnitude greater than 40 and 5.5 for hydrogen and oxygen, respectively.

TABLE 4

Latitude and longitude, estimated $\delta^2H_{dw}$ and $\delta^{18}O_{dw}$ values, measured $\delta^2H_{bw}$ and $\delta^{18}O_{bw}$ values, modeled $\delta^2H_{bw}$ and $\delta^{18}O_{bw}$ values from the 4 spatial body water models. The last column is the source for the measured $\delta^2H_{bw}$ and $\delta^{18}O_{bW}$ values. Slope, intercept and $r^2$ values at bottom of 4 columns are the results of comparing modeled $\delta^2H_{bw}$ and $\delta^{18}O_{bw}$ values with measured $\delta^2H_{bw}$ and $\delta^{18}O_{bW}$ values.

| | | | Modeled | | Measured | Modeled $\delta^2$H body water | | | | Measured | Modeled $\delta^{18}$O body water | | | |
|---|---|---|---|---|---|---|---|---|---|---|---|---|---|---|
| Location | Latitude | Longitude | $\delta^2H_{dw}$ | $\delta^{18}O_{dw}$ | $\delta^2H_{bw}$ | V_1 | V_2 | V_3 | V_4 | $\delta^{18}O_{bw}$ | V_1 | V_2 | V_3 | V_4 |
| Albuquerque, NM | 35.0844 | −106.6506 | −77 | * | −78** | −68 | −67 | −61 | −70 | NA | NA | NA | NA | NA |
| Chicago, IL | 41.8500 | −87.6500 | −48 | −6.6 | −37 ± 5 | −40 | −40 | −37 | −44 | −4.8 ± 0.6 | −4.6 | −4.5 | −4.2 | −5.5 |
| Harvard, MA | 42.5000 | −71.5833 | −57 | −8.6 | −50 ± 7 | −49 | −49 | −45 | −53 | −6.2 ± 1.4 | −6.1 | −6.1 | −5.7 | −6.9 |
| Houston, TX | 29.7631 | −95.3631 | −16 | −2.0 | −14 ± 3 | −12 | −12 | −12 | −23 | −1.4 ± 1.3 | −1.1 | −1.1 | −0.9 | −2.5 |
| Houston, TX | 29.7631 | −95.3631 | −16 | −2.0 | −13 ± 6 | −12 | −12 | −12 | −23 | 0.5 ± 1.6 | −1.1 | −1.1 | −0.9 | −2.5 |
| Jerico, VT | 44.5039 | −72.9981 | −74 | −10.6 | −67 ± 7 | −65 | −64 | −59 | −66 | −8.2 ± 1.5 | −7.8 | −7.7 | −7.3 | −8.3 |
| Madison, WI | 43.0731 | −89.4011 | −55 | −7.7 | −42 ± 5 | −47 | −46 | −43 | −50 | −5.2 ± 0.7 | −5.5 | −5.4 | −5.0 | −6.1 |
| Mt. Rainer, WA | 46.800 | −121.800 | −113 | −15.1 | −86 ± 1* | −107 | −106 | −98 | −90 | −10.3 ± 0.1 | −11.9 | −11.8 | −11.2 | −9.8 |
| | | | | | Slope | 1.09 | 1.07 | 0.99 | 0.83 | | 0.99 | 0.98 | 0.95 | 0.73 |
| | | | | | Intercept | 2.77 | 2.54 | 1.47 | −12.24 | | −0.40 | −0.40 | −0.22 | −2.23 |
| | | | | | $r^2$ | 0.92 | 0.92 | 0.91 | 0.97 | | 0.95 | 0.95 | 0.95 | 0.98 |

Example 5

Application of the Spatial Body Water Model to Distinguish Locals from Visitors

We used $\delta^2H_{bw}$ values estimated using spatial model V_1 for Houston, Chicago and Salt Lake City combined with the estimated range in body water turnover for an adult male to predict the length of time for the body water of an individual to become indistinguishable from a locals (Table 5). A visitor to Chicago was indistinguishable from locals 14 to 18 days after arrival and a visitor to Salt Lake City was indistinguishable from locals 25 to 32 days after arrival (Table 5). The difference in the length of time for the two scenarios is due to the magnitude of the difference in the $\delta^2H_{bw}$ values between the three locations. $\delta^2H_{bw}$ of a native of Chicago is 28‰ different than a native of Houston and the $\delta^2H_{bw}$ of a native of Salt Lake City is 90‰ different than a native of Houston (Table 5). As a result, the visitor to Chicago is within 4.5‰ of equilibrium values ~1 week before the visitor to Salt Lake City.

TABLE 5

Locations, $\delta^2H_{bw}$ at equilibrium, total change in $\delta^2H_{bw}$, and the estimated length of time for $\delta^2H_{bw}$ values of a person that travels from Houston to Chicago or to Salt Lake City to be indistinguishable from residents. The length of time is calculated using two half-lives (7.5 and 5.9 days) to determine the expected range in time.

| | $\delta^2H_{bw}$ | Change in $\delta^2H_{bw}$ | Time | |
|---|---|---|---|---|
| Location | ‰ | ‰ | 7.5 days | 5.9 days |
| Houston, TX | −12 | 0.0 | 0 | 0 |
| Chicago, IL | −40 | 28 | 18 | 14 |
| Salt Lake City, UT | −102 | 90 | 32 | 25 |

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A method for reconstructing a travel history for an individual, comprising:
   collecting a sample of breath exhaled by the individual;
   analyzing the sample to obtain a breath isotope ratio for at least one isotope;
   transforming the breath isotope ratio to a body water isotope ratio; and
   determining a travel origin by comparing the body water isotope ratio to a map model that correlates body water isotope ratios to geographic locations, said map model using at least one isotope source input associated with the geographic locations.

2. The method of claim 1, further comprising adjusting the body water isotope ratio using an isotope turnover model to obtain an adjusted body water isotope ratio, wherein said model includes a rate of isotope turnover and a time interval over which isotope turnover has occurred.

3. The method of claim 1, wherein the isotope is a hydrogen isotope.

4. The method of claim 1, wherein the isotope is an oxygen isotope.

5. The method of claim 1, wherein the analyzing step is performed using laser absorption spectroscopy.

6. The method of claim 1, further comprising:
   obtaining an attested travel origin provided by the individual at any point during the method; and
   comparing the travel origin to the attested travel origin subsequent to determining the travel origin.

7. The method of claim 1, wherein the isotope source input is selected from the group consisting of drinking water, food, free water in food, organic food molecules, atmospheric oxygen, water vapor, and combinations thereof.

8. The method of claim 7, wherein the input is drinking water.

9. A system for reconstructing a travel history for an individual, comprising:
- a collection device configured to collect a sample of breath exhaled by the individual;
- an analysis device configured to accept the sample of breath and provide a measurement of a breath isotope ratio for at least one isotope;
- a data processor configured to accept the measurement from the analysis device, said data processor capable of transforming each breath isotope ratio to a body water isotope ratio and comparing the body water isotope ratio to a map model that correlates body water isotope ratios to geographic locations so as to determine a travel origin for the individual; and
- an output device for communicating the travel origin.

10. The system of claim 9, wherein the data processor is also capable of adjusting each body water isotope ratio using an isotope turnover model to obtain an adjusted body water isotope ratio, wherein said model includes a rate of isotope turnover and a time interval over which isotope turnover has occurred.

11. The system of claim 9, wherein the collection device and the analysis device are a single integrated device.

12. The system of claim 9, wherein the isotope is a hydrogen isotope.

13. The system of claim 9, wherein the isotope is an oxygen isotope.

14. The system of claim 9, wherein the analysis device comprises a laser isotope analyzer.

15. The system of claim 9, wherein the output device is a computer monitor.

16. The system of claim 9, wherein the input is selected from the group consisting of drinking water, food, free water in food, organic food molecules, atmospheric oxygen, water vapor, and combinations thereof.

17. The system of claim 16, wherein the input is drinking water.

18. A non-transitory machine readable storage medium having instructions embodied thereon, the instructions being executable by a processor to determine a travel origin for an individual, comprising:
- an input module to receive isotope ratio data in the form of breath isotope ratio measurements and a time interval;
- a transformation module to transform the isotope ratio data received from the input module into body water isotope ratios, wherein said transformation module includes a body water model correlating breath isotope ratio measurements to body water isotope ratios; and
- an output module to compare the body water isotope ratio received from the transformation module to a map model correlating body water isotope ratios to geographical locations, and configured to output the travel origin to an output device.

19. The non-transitory machine readable storage medium of claim 18, further comprising an adjustment module to calculate an adjusted body water isotope ratio received from the transformation module based on isotope turnover during the time interval, wherein said adjustment module includes an isotope turnover model including a rate of isotope turnover.

20. The non-transitory machine readable storage medium of claim 18, further comprising a second transformation module to transform the body water isotope ratio received from the transformation module to at least one input isotope ratio.

21. The non-transitory machine readable storage medium of claim 18, wherein the isotope is a hydrogen isotope.

22. The non-transitory machine readable storage medium of claim 18, wherein the isotope is an oxygen isotope.

* * * * *